US012279993B2

(12) United States Patent
Becker et al.

(10) Patent No.: US 12,279,993 B2
(45) Date of Patent: Apr. 22, 2025

(54) SMART WELDING HELMET MODULES WITH ADAPTABLE HELMET DEVICES

(71) Applicant: Illinois Tool Works Inc., Glenview, IL (US)

(72) Inventors: William Joshua Becker, Manitowoc, WI (US); Mitchell James Muske, Neenah, WI (US); James Francis Rappl, Neenah, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 631 days.

(21) Appl. No.: 17/340,380

(22) Filed: Jun. 7, 2021

(65) Prior Publication Data
US 2022/0031515 A1 Feb. 3, 2022

Related U.S. Application Data

(60) Provisional application No. 63/125,097, filed on Dec. 14, 2020, provisional application No. 63/059,575, filed on Jul. 31, 2020.

(51) Int. Cl.
*A61F 9/06* (2006.01)
*G02C 7/10* (2006.01)

(52) U.S. Cl.
CPC .............. *A61F 9/067* (2013.01); *G02C 7/101* (2013.01); *G02C 7/104* (2013.01); *A41D 2600/202* (2013.01)

(58) Field of Classification Search
CPC .. A61F 9/06; A61F 9/067; A61F 9/065; A61F 9/061; A61F 9/068; G02F 2201/58; A41D 2600/202
See application file for complete search history.

(56) References Cited

U.S. PATENT DOCUMENTS

| 4,021,840 A | 5/1977 | Ellsworth |
| 4,577,796 A | 3/1986 | Powers |
| 4,641,292 A | 2/1987 | Tunnell |
| 4,733,051 A | 3/1988 | Nadeau |

(Continued)

FOREIGN PATENT DOCUMENTS

| BE | 835944 | 3/1976 |
| CA | 2725719 A1 | 6/2012 |

(Continued)

OTHER PUBLICATIONS

European Patent Office, Extended European Search Report, Application No. 21213550.3, mailed May 6, 2022, 7 pages.

(Continued)

*Primary Examiner* — Paul C Lee
(74) *Attorney, Agent, or Firm* — McAndrews, Held & Malloy, Ltd.

(57) ABSTRACT

Described herein are examples of smart helmet modules that can be affixed to conventional welding helmets. In some examples, a smart helmet module may include one or more sensors configured to detect if/when welding is occurring, and/or whether a welding helmet is being worn in an up or down position, or not at all. In some examples, a smart helmet module may include one or more helmet devices configured to automatically activate or deactivate based on whether welding is taking place and/or the welding helmet is being worn up, down, or not at all.

14 Claims, 7 Drawing Sheets

(56) References Cited

U.S. PATENT DOCUMENTS

| | | |
|---|---|---|
| 4,776,323 A | 10/1988 | Spector |
| 4,812,614 A | 3/1989 | Wang |
| 5,572,102 A | 11/1996 | Goodfellow |
| 5,796,341 A | 8/1998 | Stratiotis |
| 5,923,555 A | 7/1999 | Bailey |
| 5,932,123 A | 8/1999 | Marhofer |
| 5,978,090 A | 11/1999 | Burri |
| 6,103,994 A | 8/2000 | Decoster et al. |
| 6,209,144 B1 | 4/2001 | Carter |
| 6,242,711 B1 | 6/2001 | Cooper |
| 6,271,500 B1 | 8/2001 | Hirayama |
| 6,337,458 B1 | 1/2002 | Lepeltier |
| 6,388,422 B1 | 5/2002 | Lew |
| 6,476,581 B2 | 11/2002 | Lew |
| 6,516,289 B2 | 2/2003 | David |
| 6,624,388 B1 | 9/2003 | Blankenship et al. |
| 6,842,722 B2 | 1/2005 | David |
| 7,178,932 B1 | 2/2007 | Buckman |
| 7,457,724 B2 | 11/2008 | Vock |
| 7,534,005 B1 | 5/2009 | Buckman |
| 7,559,902 B2 | 7/2009 | Ting |
| 7,698,101 B2 | 4/2010 | Alten |
| 7,808,385 B2 | 10/2010 | Zheng |
| 7,848,860 B2 | 12/2010 | Saposnik |
| 7,926,118 B2 | 4/2011 | Becker |
| 7,962,967 B2 | 6/2011 | Becker |
| 8,099,258 B2 | 1/2012 | Alten |
| 8,274,013 B2 | 9/2012 | Wallace |
| 8,316,462 B2 | 11/2012 | Becker et al. |
| 8,502,866 B2 | 8/2013 | Becker |
| 8,569,655 B2 | 10/2013 | Cole |
| 8,599,323 B2 | 12/2013 | Chen |
| 8,605,008 B1 | 12/2013 | Prest |
| 8,680,434 B2 | 3/2014 | Stoger et al. |
| 8,915,740 B2 | 12/2014 | Zboray |
| 8,957,835 B2 | 2/2015 | Hoellwarth |
| 8,990,963 B2 | 3/2015 | Matthews et al. |
| 8,992,226 B1 | 3/2015 | Leach |
| 9,566,192 B2 | 2/2017 | Becker et al. |
| 10,610,708 B2 | 4/2020 | Awiszus et al. |
| 2001/0045639 A1 | 11/2001 | Hanamura |
| 2002/0056708 A1 | 5/2002 | Moriguchi |
| 2002/0180695 A1 | 12/2002 | Lawrence |
| 2005/0233859 A1 | 10/2005 | Takai |
| 2007/0102479 A1 | 5/2007 | Kan |
| 2007/0182709 A1 | 8/2007 | Brush |
| 2007/0187378 A1 | 8/2007 | Karakas |
| 2007/0261153 A1 | 11/2007 | Wise |
| 2008/0038702 A1 | 2/2008 | Choquet |
| 2008/0314887 A1 | 12/2008 | Stoger |
| 2008/0318679 A1 | 12/2008 | Tran |
| 2009/0057286 A1 | 3/2009 | Ihara |
| 2009/0231423 A1 | 9/2009 | Becker et al. |
| 2009/0276930 A1 | 11/2009 | Becker |
| 2009/0298024 A1 | 12/2009 | Batzler |
| 2010/0035688 A1 | 2/2010 | Picunko |
| 2010/0154255 A1 | 6/2010 | Robinson |
| 2010/0223706 A1 | 9/2010 | Becker |
| 2011/0117527 A1 | 5/2011 | Conrardy |
| 2011/0220619 A1 | 9/2011 | Mehn |
| 2011/0316516 A1 | 12/2011 | Schiefermuller |
| 2012/0012561 A1 | 1/2012 | Wiryadinata |
| 2012/0050688 A1 | 3/2012 | Wu |
| 2012/0057240 A1 | 3/2012 | Sundell |
| 2012/0085741 A1 | 4/2012 | Holverson et al. |
| 2013/0081293 A1 | 4/2013 | Delin |
| 2013/0112673 A1 | 5/2013 | Petrilla et al. |
| 2013/0206740 A1 | 8/2013 | Pfeifer |
| 2013/0206741 A1 | 8/2013 | Pfeifer et al. |
| 2013/0208569 A1 | 8/2013 | Pfeifer |
| 2013/0215281 A1 | 8/2013 | Hobby |
| 2013/0291271 A1 | 11/2013 | Becker |
| 2014/0059730 A1 | 3/2014 | Kim |
| 2014/0069900 A1 | 3/2014 | Becker |
| 2014/0134579 A1 | 5/2014 | Becker |
| 2014/0134580 A1 | 5/2014 | Becker |
| 2014/0185282 A1 | 7/2014 | Hsu |
| 2014/0205976 A1 | 7/2014 | Peters |
| 2014/0263224 A1 | 9/2014 | Becker |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2015/0009316 A1 | 1/2015 | Baldwin |
| 2015/0072323 A1 | 3/2015 | Postlethwaite |
| 2015/0125836 A1 | 5/2015 | Daniel |
| 2015/0154884 A1 | 6/2015 | Salsich |
| 2015/0248845 A1 | 9/2015 | Postlethwaite |
| 2016/0022496 A1 | 1/2016 | Dekeuster et al. |
| 2016/0089751 A1 | 3/2016 | Batzler et al. |
| 2017/0143549 A1 | 5/2017 | Becker et al. |
| 2018/0271709 A1 | 9/2018 | Currie |
| 2018/0360663 A1* | 12/2018 | Hsieh .................. G02F 1/13306 |
| 2020/0085132 A1* | 3/2020 | Segura ...................... A61F 9/06 |

FOREIGN PATENT DOCUMENTS

| | | | |
|---|---|---|---|
| CN | 2176193 | 9/1994 | |
| CN | 1093961 | 10/1994 | |
| CN | 1130116 | 9/1996 | |
| CN | 1266391 | 9/2000 | |
| CN | 1633345 | 6/2005 | |
| CN | 1665634 | 9/2005 | |
| CN | 1780712 | 5/2006 | |
| CN | 101068648 | 11/2007 | |
| CN | 101108439 | 1/2008 | |
| CN | 101352778 | 1/2009 | |
| CN | 101422839 | 5/2009 | |
| CN | 201249320 | 6/2009 | |
| CN | 102341950 | 2/2012 | |
| CN | 102971106 | 3/2013 | |
| CN | 103128425 | 6/2013 | |
| CN | 104902858 A * | 9/2015 | ............... A61F 9/06 |
| CN | 108524099 A * | 9/2018 | ............. A42B 3/225 |
| DE | 102005032136 | 1/2007 | |
| EP | 2022592 A1 | 2/2009 | |
| EP | 2082656 A1 | 7/2009 | |
| ES | 336308 | 1/1968 | |
| JP | 10305366 | 11/1998 | |
| JP | 2016059094 | 4/2016 | |
| KR | 950003258 | 4/1995 | |
| KR | 101237675 | 8/2012 | |
| WO | 9934950 | 7/1999 | |
| WO | 2005084867 | 9/2005 | |
| WO | 2006042572 A1 | 4/2006 | |
| WO | 2007009131 | 1/2007 | |
| WO | 2008101379 A1 | 8/2008 | |
| WO | 2009137379 A1 | 11/2009 | |
| WO | 2019051349 | 3/2019 | |

OTHER PUBLICATIONS

Fronius, Vizor Connect, retrieved from https://www.fronius.com/en/welding-technology/products/accessories/personal-protective-equipment/automatic-protective-welding-helmets/vizor-connect/vizor-connect, retrieved on Nov. 18, 2021, 5 pages.

Trafimet welding and cutting, T-Link System is the new technology granting total eye protection for the welding operator, retrieved from http://www.trafimet.com/welding-systems/t-link-eye-protection-system-for-welders/, retrieved on Nov. 18, 2021, 11 pages.

European Patent Office, Extended European Search Report, Application No. 21185906, mailed Dec. 23, 2021.

Canada Patent Office, Office Action, Application No. 3,123,077, mailed Jul. 25, 2024, 4 pages.

Kevin Dixon, et al., Gesture-based Programming for Robotic Arc Welding, Carnegie Mellon University, dated Dec. 6, 2002 (24 pages).

International Search Report and Written Opinion for PCT/US2016/013867, dated Apr. 28, 2016 (11 pages).

Li, Larry, Time-of-Flight Camera—An Introduction, Technical White Paper, SLOA190B—Jan. 2014, revised May 2014 (10 pages).

(56) References Cited

OTHER PUBLICATIONS

Heston, Tim, Lights, camera, lean-recording manufacturing efficiency, The Fabricator, Aug. 2010 (4 pages).
Intelligenter SchweiBbrenner, Intelligent Welding Torch, IP Bewertungs AG (IPB) (12 pages), Cited in US Pre-grant Publication 2016/0193679 filed on Jul. 7, 2016.
Intelligent Robotic Arc Sensing, Lincoln Electric, Oct. 20, 2014, http://www.lincolnelectric.com/en-us/support/process-and-theory/pages/intelligent-robotic-detail.aspx (3 pages).
LiveArc Welding Performance Management System, A reality-based recruiting, screening and training solution, MillerWelds.com 2014 (4 pages).
Handheld Welding Torch with Position Detection technology description, Sep. 21, 2011 (11 pages).
Frank Shaopeng Cheng (2008). Calibration of Robot Reference Frames for Enhanced Robot Positioning Accuracy, Robot Manipulators, Marco Ceccarelli (Ed.), ISBN: 978-953-7619-06-0, InTech, Available from: http://www.intechopen.com/books/robot_manipulators/calibration_of_robot_reference_frames_for_enhanced_r obot_positioning_accuracy (19 pages).
Lutwak, Dr. Robert, Micro-Technology for Positioning, Navigation, and Timing Towards PNT Everywhere and Always Stanford PNT Symposium, Stanford, CA Oct. 29, 2014 (26 pages).
Lutwak, Dr. Robert, DARPA, Microsystems Tech. Office, Micro-Technology for Positioning, Navigation, and Timing Towards PNT Everywhere and Always, Feb. 2014 (4 pages).
Parnian, Neda et al., Integration of a Multi-Camera Vision System and Strapdown Inertial Naviation System (SDINS) with a Modified Kalman Filter, Sensors 2010,10, 5378-5394; doi: 10.3390/s100605378 (17 pages).
Pipe-Bug, Motorized & Manual Chain Driven Pipe Cutting Machines From Bug-0 Systems (4 pages), Publically available at least on Oct. 12, 2008 according to Wayback Machine.
Electronic speckle pattern interferometry Wikipedia, the free encyclopedia (4 pages), [retrieved Feb. 10, 2015].
Rivers, et al., Position-Correcting Tools for 2D Digital Fabrication (7 pages), Jul. 1, 2012.
Wavelength Selective Switching, http://en.wikipedia.org/wiki/wavelength_selective_switching, Mar. 4, 2015 (5 pages).
Cavilux HF, Laser Light for High-Speed Imaging, See What You Have Missed (2 pages), Publically available at least on Apr. 11, 2021 according to Wayback Machine.
Cavilux Smart, Laser Light for Monitoring and High Speed Imaging, Welcome to the Invisible World (2 pages), Publically available at least on Jan. 18, 2021 according to Wayback Machine.
Windows 10 to Get 'Holographic' Headset and Cortana, BBC News, www.bbc.com/news/technology-30924022, Feb. 26, 2015 (4 pages).
Daqri Smart Helmet, The World's First Wearable Human Machine Interface, Brochure (9 pages), Publically available for sale in 2016.
International Search Report from PCT application No. PCT/US2015/041044, dated Nov. 16, 2015, 15 pgs.
"CyberGlove Data Glove: User Guide," CyberGlove Systems LLC, Dec. 2007, http://www.cyberglovesystems.com/support/; http://static1.squarespace.com/static/559c381ee4b0ff7423b6b6a4/t574f4b392eeb81ec9526760f/1464814396021/CyberGloveUserGuid_wired_rev10.pdf.
"CyberGlove II Wireless Data Glove: User Guide," CyberGlove Systems LLC, Jul. 2008, http://www.cyberglovesystems.com/support/; https://static1.squarespace.com/static/559c381ee4b0ff7123b6b6a4/t/574f4c35b654f981724d1927/1464814655198/CyberGlovell_UserGuide_2009_0.pdf.
International Search Report for application No. PCT/US2011/043757 mailed Nov. 8, 2011.
Canadian Office Action Appln No. 2,831,295 dated Sep. 19, 2018 (5 pages).
Lincoln Electric, "Power Wave Manager user Manual", pp. 26-27, http://lincolnelectric.com/en-za/equipment/Documents/Power-WaveManager.pdf, Jan. 25, 2011.
Canadian Office Action Appln No. 2,831,295 dated Nov. 6, 2017 (4 pages).
ESAB, "PEK Control panel," pp. 7-8, http://pdfmanuals.esab.com/private/Library/InstructionManuals/0460%20949%20174%20GB.pdf, 2009.
Int'l Search Report and Written Opinion Appln. No. PCT/US2019/051475 mailed Nov. 27, 2019 (11 pgs).

\* cited by examiner

SMART WELDING HELMET MODULES WITH ADAPTABLE HELMET DEVICES

CROSS REFERENCE TO RELATED APPLICATIONS

This application claims priority to, and the benefit of, U.S. Provisional Application No. 63/059,575, filed Jul. 31, 2020, entitled "SMART WELDING HELMET MODULES WITH ADAPTABLE LENSES, LIGHTING, AND ACTIVATION STATES," and U.S. Provisional Application No. 63/125,097, filed Dec. 14, 2020, entitled "SMART WELDING HELMETS WITH ARC TIME TRACKING VERIFICATION AND LENS MAINTENANCE DETECTION," the entire contents of which are hereby incorporated by reference.

TECHNICAL FIELD

The present disclosure generally relates to welding helmets and, more particularly, to smart welding helmet modules with adaptable helmet devices.

BACKGROUND

Welding is a significant source of both light and spatter. Welding helmets are worn during welding to shield the heads of operators from the spatter. Light filters within the welding helmet attenuate the brightness of the light so operators can still see what they are doing while welding.

Limitations and disadvantages of conventional and traditional approaches will become apparent to one of skill in the art, through comparison of such systems with the present disclosure as set forth in the remainder of the present application with reference to the drawings.

BRIEF SUMMARY

The present disclosure is directed to smart welding helmet modules with adaptable lenses, lighting, and activation states, substantially as illustrated by and/or described in connection with at least one of the figures, and as set forth more completely in the claims.

These and other advantages, aspects and novel features of the present disclosure, as well as details of an illustrated example thereof, will be more fully understood from the following description and drawings.

BRIEF DESCRIPTION OF THE DRAWINGS

The figures are not necessarily to scale. Where appropriate, the same or similar reference numerals are used in the figures to refer to similar or identical elements.

DETAILED DESCRIPTION

Figure 1:
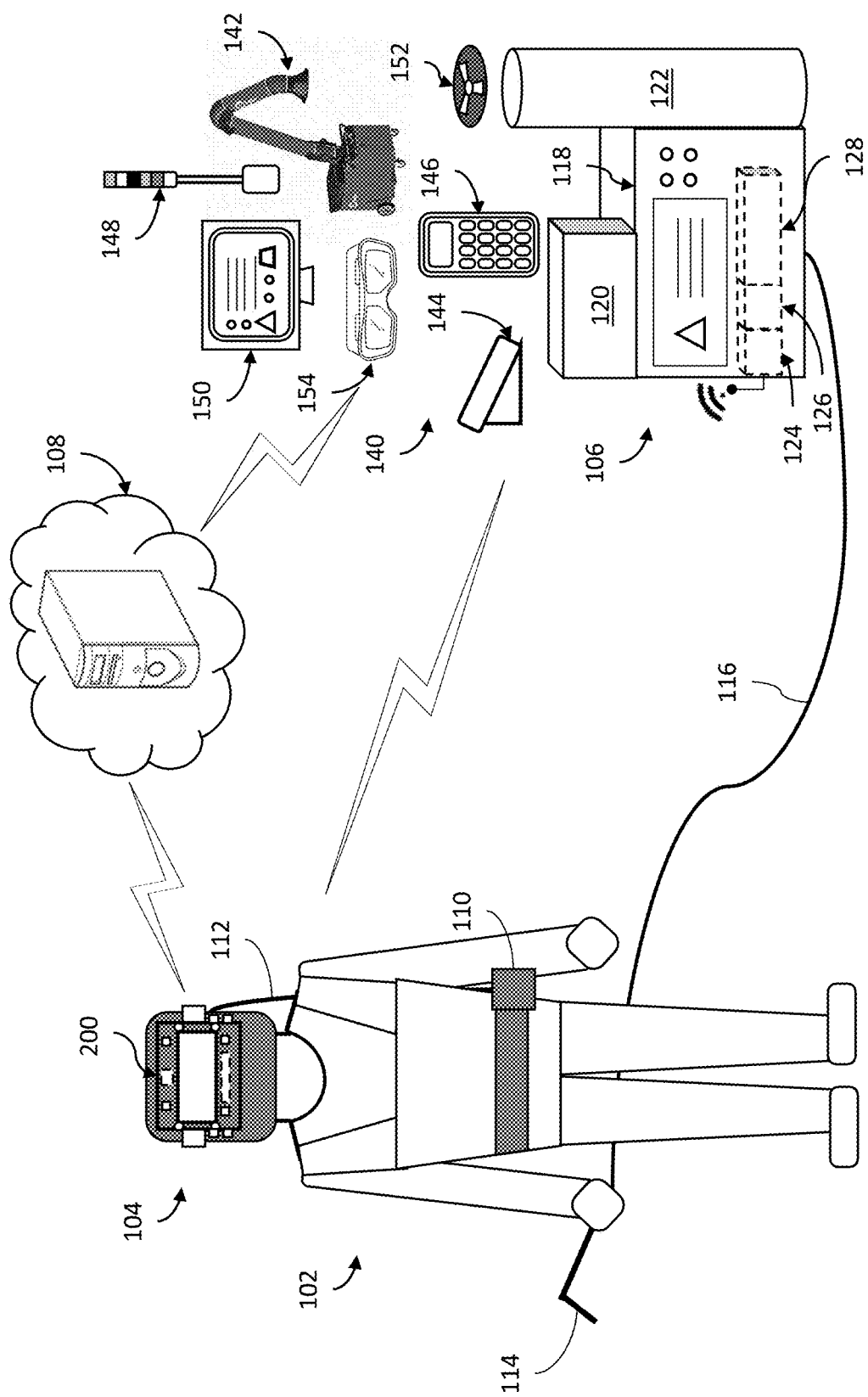
FIG. 1 shows an example of an operator wearing a welding helmet with a smart helmet module, in accordance with aspects of this disclosure.

Some examples of the present disclosure relate to smart helmet modules that can be affixed to conventional welding helmets. In some examples, a smart helmet module may include one or more sensors configured to detect if/when welding is occurring, a welding helmet is being worn by an operator, and/or whether the helmet is in an up or down position. In some examples, a smart helmet module may include certain helmet devices (e.g., lights) configured to automatically activate/deactivate based on whether welding is taking place and/or whether the helmet is being worn up, down, or not at all. In some examples, a smart module may be configured to identify the operator wearing the helmet, and automatically configure certain aspects of the helmet accordingly (e.g., adaptable lens configuration, intensity of lights, state of smart helmet module when helmet worn up/down or not worn, etc.).

Some examples of the present disclosure relate to a welding helmet, comprising: a light; a sensor configured to detect a worn status of the welding helmet, the sensor configured to output a sensor signal representative of the worn status; and processing circuitry configured to: determine, based on the sensor signal, the worn status of the welding helmet, the worn status being indicative of the welding helmet being worn, worn in a raised position, worn in a lowered position, or not worn, activate the light when the worn status is indicative of the welding helmet being worn in the raised position, and deactivate the light when the worn status is indicative of the welding helmet being worn in the lowered position.

In some examples, the sensor comprises a thermal sensor, a switch sensor, an optical sensor, a reed switch, a capacitive sensor, a carbon dioxide sensor, an oxygen sensor, a potentiometer, an encoder, or an accelerometer. In some examples, the welding helmet further comprises a power source configured to provide power to the light, the processing circuitry being further configured to configure the power source, or the provision of power from the power source, based on the worn status. In some examples, the welding helmet further comprises a visor lens, the visor lens comprising an adaptable lens, and the visor lens configured to adjust a focal length or radius of curvature of the adaptable lens.

In some examples, the processing circuitry is further configured to identify an identity of an operator wearing the welding helmet, the visor lens configured to adjust the focal length or radius of curvature of the adaptable lens based on the identity of the operator. In some examples, the welding helmet further comprises one or more control inputs, the one or more control inputs being configured to receive an operator input, and the visor lens configured to adjust the focal length or radius of curvature of the adaptable lens based on the operator input. In some examples, the welding helmet further comprises a helmet shell and a smart helmet module, the smart helmet module comprising the sensor, the light, the processing circuitry, and a mechanical linkage configured for removable attachment to the helmet shell, the mechanical linkage configured to allow the smart helmet module to move relative to the helmet shell while still remaining attached to the helmet shell.

Some examples of the present disclosure relate to a welding helmet, comprising: a user interface comprising one or more input devices and one or more output devices; a visor lens comprising an adaptable lens, a display screen, or an auto-darkening filter; a sensor configured to detect a worn status of the welding helmet, the sensor configured to output a sensor signal representative of the worn status; and processing circuitry configured to: determine, based on the sensor signal, the worn status of the welding helmet, the worn status being indicative of the welding helmet being worn, worn in a raised position, worn in a lowered position, or not worn, and configure the visor lens, the one or more input devices, or a speaker of the one or more output devices based on the worn status.

In some examples, the welding helmet further comprises a power source configured to provide power to the user interface, the visor lens, or the sensor, the processing circuitry being further configured to configure the power source, or the provision of power from the power source, based on the worn status. In some examples, the visor lens comprises the adaptable lens, and the visor lens is configured to adjust a focal length or radius of curvature of the adaptable lens. In some examples, the processing circuitry is further configured to identify an identity of an operator wearing the welding helmet, the visor lens configured to adjust the focal length or radius of curvature of the adaptable lens based on the identity of the operator.

In some examples, the welding helmet further comprises one or more control inputs, the one or more control inputs being configured to receive an operator input, and the visor lens configured to adjust the focal length or radius of curvature of the adaptable lens based on the operator input. In some examples, the sensor comprises a first sensor, and the processing circuitry is configured to determine whether welding is occurring based on a sensor signal of a second sensor, a darkened or undarkened state of an auto-darkening filter (ADF), tool data received from a welding-type tool, or welding data received from welding-type equipment. In some examples, the welding helmet further comprises a helmet shell and a smart helmet module, the smart helmet module comprising the sensor, the user interface, the visor lens, the processing circuitry, and a mechanical linkage configured for removable attachment to the helmet shell, the mechanical linkage configured to allow the smart helmet module to move relative to the helmet shell while still remaining attached to the helmet shell.

Some examples of the present disclosure relate to a welding helmet, comprising: a sensor configured to detect a worn status of the welding helmet, the sensor configured to output a sensor signal representative of the worn status; and processing circuitry configured to: determine, based on the sensor signal, the worn status of the welding helmet, the worn status being indicative of the welding helmet being worn, worn in a raised position, worn in a lowered position, or not worn, configure a helmet device of the welding helmet, or a welding device in communication with the welding helmet, based on the worn status, the helmet device comprising a cooling device of the welding helmet, a speaker of the welding helmet, an input device of the welding helmet, a visor lens of the welding helmet, a camera of the welding helmet, or a power source of the welding helmet.

In some examples, the welding device comprises a welding-type power supply, a wire feeder, a powered air purifying respirator (PAPR) connected to the welding helmet, a welding pendant, a foot pedal, a welding torch, a fume extractor, electronic eyewear, a remote display, a cooling system, a remote beacon, or a welding guidance system. In some examples, the welding helmet further comprises communication circuitry, the processing circuitry configured to configure the welding device via one or more signals sent to the welding device via the communication circuitry. In some examples, the sensor comprises a thermal sensor, a switch sensor, an optical sensor, a reed switch, a capacitive sensor, a carbon dioxide sensor, an oxygen sensor, a potentiometer, an encoder, or an accelerometer.

In some examples, the processing circuitry is configured to deactivate or limit operation of the helmet device when the worn status is indicative of the welding helmet being worn in the raised position or not worn. In some examples, the welding helmet comprises the cooling device, the input device, the speaker, or the visor lens, the sensor comprises a first sensor, the sensor signal comprises a first sensor signal, and the processing circuitry is configured to determine whether welding is occurring based on a second sensor signal of a second sensor, a darkened or undarkened state of an auto-darkening filter (ADF), tool data received from a welding-type tool, or welding data received from welding-type equipment, the processing circuitry configured to configure the helmet device based on the worn status and whether welding is occurring.

FIG. 1 shows an example of a welding operator 102 wearing a welding helmet 104 fitted with a smart helmet module 200. As shown, the welding helmet 104 is in communication (e.g., via smart helmet module 200) with welding equipment 106, one or more welding accessories 140, and one or more remote servers 108. In some examples, the welding helmet 104 may also be in communication with a powered air purifying respirator (PAPR) 110 (and/or other respirator) connected to the welding helmet 104 via hose 112, and/or a welding torch 114. In some examples, some or all of the communication may be through a local and/or wide area network.

While referred to as remote, in some examples one or more of the remote servers 108 may be nearby computers. While referred to as a welding torch 114, in some examples the welding torch 114 may be a different type of tool. For example, a tool configured for welding, cladding, brazing, plasma cutting, induction heating, laser (including laser welding, laser hybrid, and laser cladding), carbon arc cutting or gouging, and/or resistive preheating. As shown, the welding torch 114 is connected to the welding equipment 106 via cable 116.

In the example of FIG. 1, the welding equipment 106 comprises a welding-type power supply 118, wire feeder 120, and gas supply 122. As shown, the power supply 118 includes communication circuitry 124, control circuitry 126, and power conversion circuitry 128 interconnected with one another. In some examples, the communication circuitry 124 may be configured for communication with the remote server(s) 108, welding torch 114, and/or the welding helmet 104. In some examples, the power conversion circuitry 128 may be configured to receive input power (e.g., from a generator, a battery, mains power, etc.) and convert the input power to welding-type output power, such as might be suitable for use by the welding torch 114 for welding-type operations, for example. In some examples, the control circuitry 126 may be configured to control operation of the communication circuitry 124, power conversion circuitry 128, wire feeder 120, and/or gas supply 122 (e.g. via one or more control signals). In some examples, the control circuitry 126 may control communications of the welding equipment 106 with the smart helmet module 200.

In the example of FIG. 1, the welding accessories 140 include a fume extractor 142, a foot pedal 144, a welding pendant 146, a remote beacon 148, a remote display screen 150, a remote cooling system 152, and electronic eyewear 154. In some examples, the PAPR 110 and/or welding torch 114 may also be considered a welding accessory 140. In some examples, one or more of the welding accessories 140 may include control circuitry configured to control the device, and/or communication circuitry configured to facilitate communication with the welding equipment 106, smart helmet module 200, and/or other welding accessories 140.

In some examples, the fume extractor 142 may be comprise a blower or fan configured to create a negative draft that pulls lingering gases and/or airborne residues (e.g., generated during welding-type operations) into a contained filtration system of the fume extractor 142. In some examples, the foot pedal 144 may be configured to activate a welding-type operation in response to receipt of a threshold amount of pressure (e.g., via a foot pressing on the pedal 144). In some examples, the foot pedal 144 may activate the welding-type operation via transmission of a communication signal to the welding-type equipment 106 (e.g., via a wired or wireless connection) representative of an activation command. In some examples, the welding pendant 146 may be a remote control device 102 that allows an operator to control welding parameters and/or operations of the welding-type equipment 106 via communication with the welding-type equipment 106.

In some examples, the remote beacon 148 may be configured to broadcast one or more visual, invisible, audible, and/or inaudible signals to the surrounding area. For example, the signal(s) may be electromagnetic, optical within or outside the visible light spectrum (e.g., infrared, ultraviolet, etc.), and/or audio within or outside the audible frequency range (e.g., infrasonic, ultrasonic, etc.). In some examples, the signal(s) may be detectable by certain devices (e.g., other welding accessories 140), perceivable by the operator 102, and/or representative of a notification that welding is occurring or not occurring. In some examples, the remote beacon 148 may comprise a stack light with a variety of different (e.g., color, shape, size, etc.) lights that may be illuminated in various ways based on one or more received signals.

In some examples, the remote display screen 150 may be configured to show certain information to the operator 102, such as, for example, guidance as to what welds to perform in what way (e.g., with respect to location, order, position, welding parameters, etc.). In some examples, the remote display screen 150 may display warnings and/or notifications to others in the nearby area. In some examples, the remote display screen 150 may include speakers and/or output audio information along with visual information.

In some examples, the remote cooling system 152 may be configured to cool the operator 102, welding equipment 106, and/or one or more welding accessories 140 (e.g., during welding operations). In some examples, the remote cooling system 152 may integrated into apparel (e.g., a vest, apron, etc.) worn by the operator 102. While, in the example of FIG. 1, the remote cooling system 152 is depicted as a fan, in some examples the remote cooling system 152 may comprise liquid coolant, a liquid coolant circulation system, and/or other appropriate cooling mechanisms.

In some examples, the electronic eyewear 154 may comprise smart glasses, a virtual reality headset, electronic goggles, and/or other appropriate devices. In some examples, the electronic eyewear 154 may include one or more display screens (e.g., similar to the display screen(s) 216 described below). In some examples, the electronic eyewear 154 may be worn by the operator 102 behind the welding helmet 104 and/or smart helmet module 200.

Figure 2A:
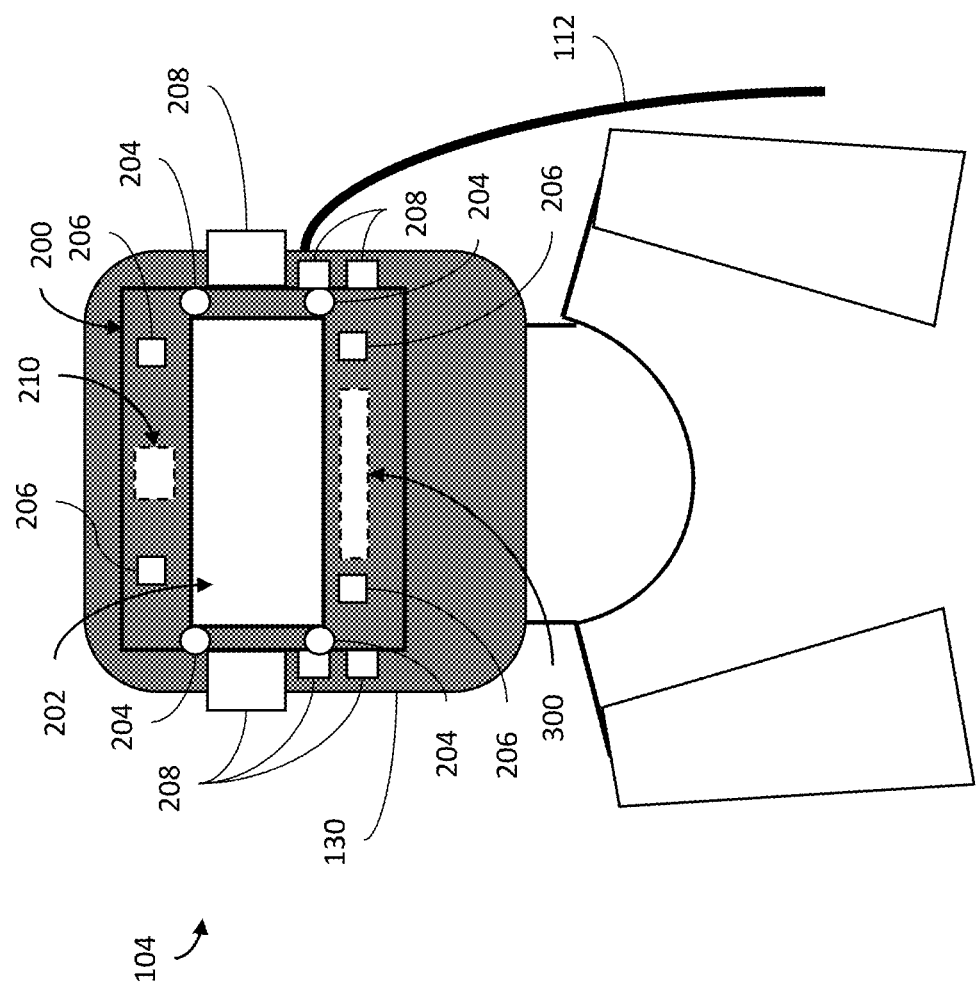
FIG. 2a shows an enlarged view of the smart helmet module of FIG. 1, in accordance with aspects of this disclosure.
Figure 2C:
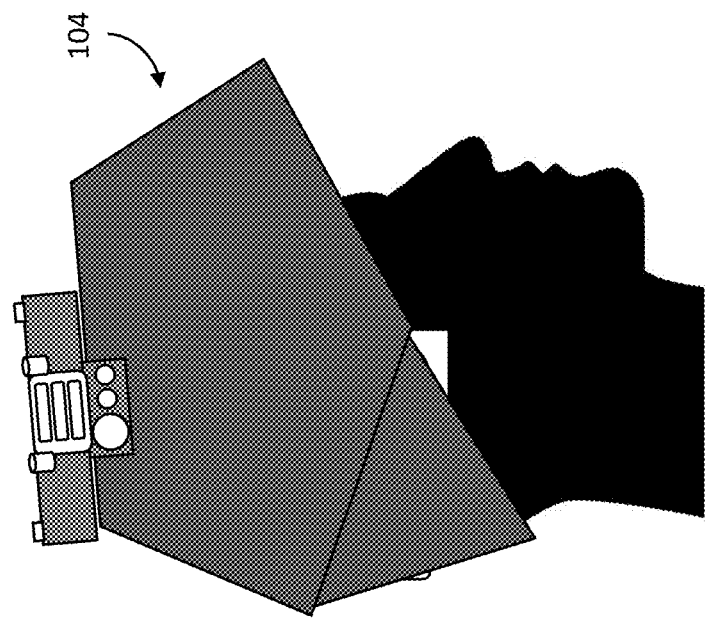
FIGS. 2b-2c show side views of the example welding helmet and smart welding module of FIG. 1 in lowered and raised positions, respectively, in accordance with aspects of this disclosure.
Figure 2B:
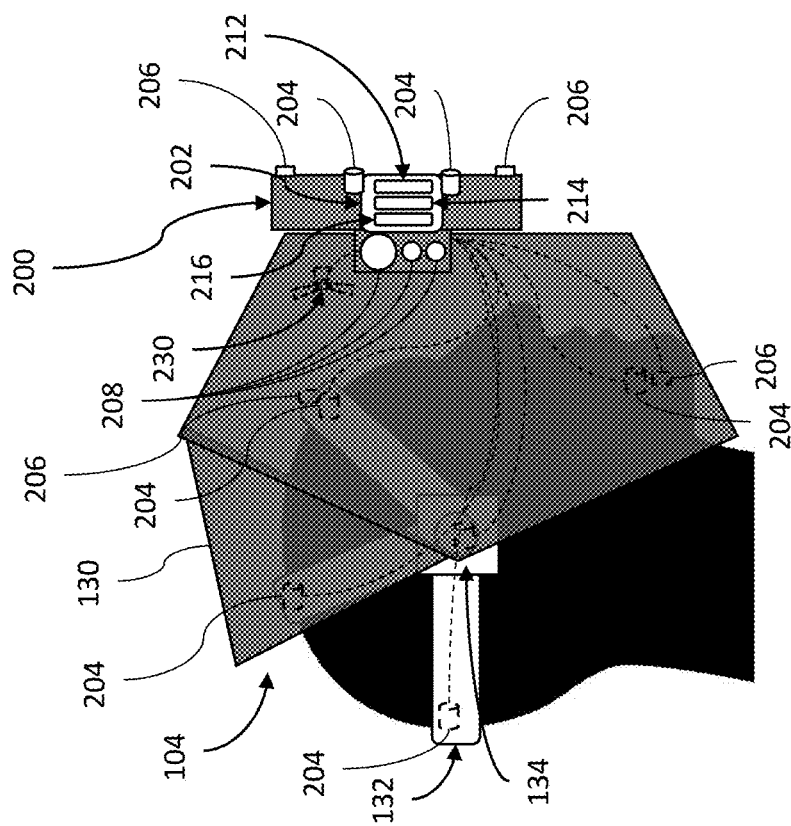

FIGS. 2a-2d shows enlarged depictions of the example welding helmet 104 and smart helmet module 200 of FIG. 1. As best shown in the example of FIG. 2b, the welding helmet 104 comprises a helmet shell 130 attached to a suspension 132. In some examples, the helmet shell 130 may have one or more apertures and/or windows on the sides of the helmet shell 130. As shown, the suspension 132 comprises several straps and/or bands configured to wrap around the crown of the head of an operator 102. The straps are connected to one another and to the helmet shell 130 at least at two side attachment points 134 on either side of the head of the operator 102. As shown in the examples of FIGS. 2b-2c, the welding helmet 104 may be configured to rotate and/or pivot about the side attachment points 134 to transition between raised and lowered positions.

In the examples of FIGS. 2a-2d, the helmet shell 130 retains the smart helmet module 200. In some examples, the smart helmet module 200 may be configured for removable attachment to the helmet shell 130. In some examples, the smart helmet module 200 may be configured for removable attachment to any number of different helmet shells 130. That is, the smart helmet module 200 may be configured for easy removal from one helmet shell 130 and attached to a different helmet shell 130, with no (or trivial) damage. In some examples, the smart helmet module 200 may be configured to be attached to the helmet shell 130 through an opening in the helmet shell 130 (such as shown, for example, in FIG. 2d). In some examples, a front lens and/or panel of the helmet shell 130 may be removed to produce such an opening in the helmet shell 130.

Figure 2D:
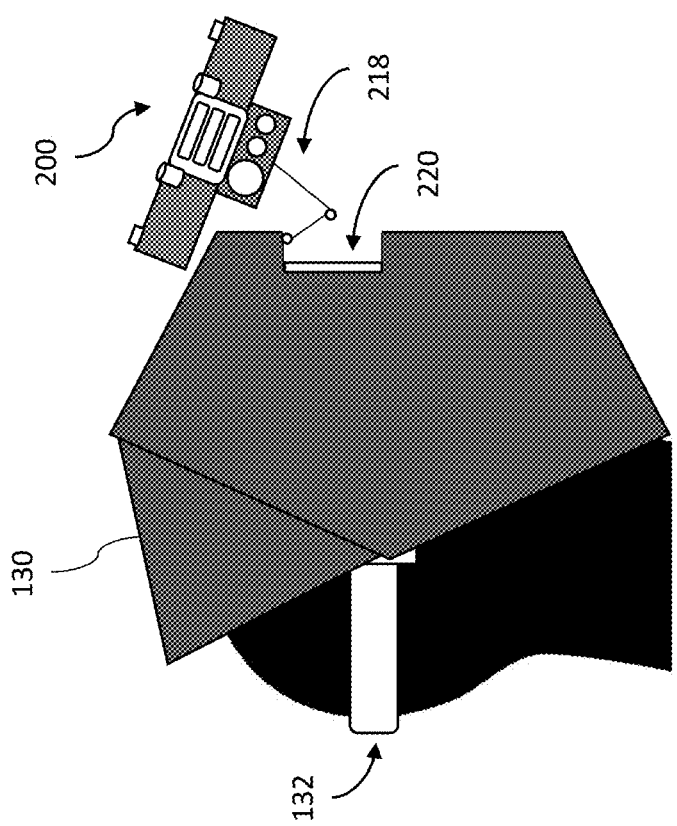
FIG. 2d shows a side view of the example welding helmet in a lowered position while the smart helmet module is in a raised position, in accordance with aspects of this disclosure.

As shown in the example of FIGS. 2b and 2d, the smart helmet module 200 may be configured to rotate, pivot, and/or otherwise move away from the helmet shell 130, while remaining attached to the helmet shell 130, such as via the folding attachment arm 218 shown in FIG. 2d. While shown as pivoting upwards via an attachment arm 218 in FIG. 2d, in some examples, the smart module 200 may instead pivot downwards, open away laterally (e.g., like a door), slide away, and/or otherwise move relative to the helmet shell 130, while remaining attached to the helmet shell 130.

In some examples, a transparent faceplate 220 may be attached to (and/or retained by) the helmet shell 130 in the opening, behind the smart helmet module 200, so that the operator 102 can have a clear (yet protected) view of the environment after moving away the smart helmet module 200. In some examples, the transparent faceplate 220 may comprise a permanently darkened lens that acts as a passive light filter to protect the eyes of an operator 102 during welding operations while still allowing the operator 102 to view the welding operations. In some examples, the transparent faceplate may comprise an auto-darkening filter (ADF) with a transparency that varies based on a signal provided by a photodiode sensor (e.g., of the ADF) configured to detect the light of a welding arc.

In the example of FIGS. 2a-2b, the smart helmet module 200 includes a visor lens 202, several sensors 204, multiple lights 206, a plurality of control inputs 208 (e.g., knobs, buttons, levers, switches, touch screens, microphones, etc.), a fan 230, module circuitry 300 (e.g., to control the above components), and a power source 210 (e.g., to power the above components). While described as control inputs 208, in some examples, the control inputs 208 may also comprise output devices, such as, for example, audio output devices (e.g., speaker(s)) and/or haptic output devices. In some examples, the visor lens 202 may be considered an output device of the smart helmet module 200. In some examples, the control inputs 208 may be configured to receive input from the operator 102, through which the operator 102 may control various aspects of the visor lens 202, sensors 204, lights 206, fan 230, module circuitry 300, power source 210, and/or smart helmet module 200.

While shown as being retained at certain positions on an external surface of the smart helmet module 200 in the example of FIGS. 2a-2b, in some examples, one or more sensors 204, lights 206, and/or control inputs 208 (e.g., microphones) may also be retained at different external positions, and/or at/on an internal surface of the smart module 200. As shown in FIG. 2b, sensors 204 and/or lights 206 may also be positioned within the helmet shell 130, retained by (and/or tethered to) the suspension 132, and/or tethered to the smart helmet module 200. In some examples, one or more lights 206 may be tethered to the smart helmet module 200 and clipped to the bottom (or other part) of helmet shell 130 (e.g., to provide a light 206 that would help the operator 102 see when the helmet is raised). While a certain number of sensors 204 and/or lights 206 are shown retained by the suspension 132 within the helmet shell 130 in the example of FIG. 2b, in some examples more or less sensors 204 and/or lights 206 may be so situated (and/or otherwise situated) within the welding helmet 104.

In some examples, one or more of the sensors 204 may comprise an optical sensor (e.g., a camera), an inertial measurement unit (IMU) (e.g., comprising an accelerometer and/or gyroscope), a photodiode sensor, a capacitive sensor, an infra-red (IR) sensor, an acoustic sensor, an induction sensor, a motion sensor, an opacity sensor, a proximity sensor, an inductive sensor, a magnet, a magnetic sensor, a GPS sensor, a heat sensor, a thermocouple, a thermistor, a photoelectric sensor, an ultrasonic sensor, an electromagnetic sensor, an inclinometer, a force sensor, a piezoelectric sensor, a chemical sensor, an ozone sensor, a smoke sensor, a magnetometer, a carbon dioxide detector, a carbon monoxide detector, an oxygen sensor, a glucose sensor, an altimeter, an object detector, a marker detector, a laser rangefinder, a sonar, a heart rate sensor, a current sensor, a voltage sensor, a power sensor, a mechanical switch, a reed switch, a potentiometer, an (e.g., optical) encoder, and/or a gaze tracker. Further descriptions of applicable sensors 204 that may be used in and/or with the smart helmet module 200 are described in U.S. Pat. No. 10,448,692, issued on Oct. 22, 2019, the entirety of which is hereby incorporated by reference.

In some examples, one or more of the sensors 204 may be used to detect whether the helmet is being worn raised, lowered, or not at all. In some examples, one or more of the sensors 204 may be used to automatically identify an operator 102 wearing the welding helmet 104. In some examples, one or more of the sensors 204 (e.g., optical sensor(s)) may be used to record images/videos, and/or transmit recordings (e.g., for later playback and/or review), of welds, welding operations, and/or other activities, operations, and/or events occurring in the surrounding environment, such as described, for example, in U.S. Pat. No. 10,380,911, issued on Aug. 13, 2019, the entirety of which is hereby incorporated by reference. In some examples, one or more of the sensors 204 (e.g., optical sensor(s)) may be used to capture images/videos which may be displayed on a display screen 216 of the smart helmet module 200 (and/or the electronic eyewear 154). While eight sensors are shown in the examples of FIGS. 2a-2d, in some examples, more or fewer sensors 204 may be used.

In the example of FIGS. 2a-2b, the smart helmet module 200 includes five lights 206. In some examples, more or fewer lights 206 may be included. In some examples, the lights 206 may be used to illuminate the surrounding environment so that the operator 102 can better see. In some examples, one or more of the lights 206 may be manually activated/deactivated by the operator 102 (e.g., via the control inputs 208). In some examples, one or more of the lights 206 may be automatically activated/deactivated (e.g., in response to one or more control signals from the module circuitry 300). For example, one or more lights 206 may be automatically activated when the welding helmet 104 is being worn down/lowered over the operators face (as shown, for example, in FIGS. 2a-2b and 2d), the ambient lighting in the environment is below a certain threshold, and/or no welding is taking place. As another example, one or more lights 206 may be automatically deactivated when the welding helmet 104 is not being worn, being worn in the up/raised position, and/or when the ambient lighting in the environment is above a certain threshold (e.g., when a welding arc is present). As yet another example, a light 206 retained within the helmet shell 130 (e.g., by suspension 132), may automatically activate when the welding helmet 104 is worn in the raised position, and deactivate when the welding helmet 104 is worn in the lowered position.

In the example of FIG. 2b, the smart helmet module 200 includes a fan 230. As shown, the fan 230 is extended away from the smart helmet module 200 within the helmet shell 130. In some examples, the fan 230 may also be retracted within the smart helmet module 200 (e.g., when the module 200 is removed or moved away from the helmet shell 130, such as shown in the example of FIG. 2d). In some examples, the fan 230 may be configured to propel air over a head of the operator 102 while the operator 102 is wearing the welding helmet 104, thereby cooling the operator 102. In some examples, the fan 230 may additionally, or alternatively, include liquid coolant and/or a liquid coolant circulation system (e.g., sprayer). While one fan 230 is shown in the example of FIG. 2b, in some examples, the smart helmet module 200 may include multiple fans 230.

In the example of FIGS. 2b-2c, the visor lens 202 is positioned in the welding helmet 104 at approximately eye level. In some examples, the visor lens 202 may be configured to allow an operator 102 to see through the visor lens 202 and view the surrounding environment. As shown in the example of FIG. 2b, the visor lens 202 includes an auto-darkening filter (ADF) 212, an adaptable lens 214, and a display screen 216. While shown in a particular arrangement in the example of FIG. 2b, in some examples, the ADF 212, adaptable lens 214, and display screen 216 may be arranged differently. In some examples, the ADF 212, adaptable lens 214, and/or display screen 216 may be removed entirely.

In some examples, the ADF 212 comprises a lens with a transparency that varies based on a signal provided by a photodiode sensor 204 configured to detect the light of a welding arc. In some examples, the signal may instead be provided by the smart module circuitry 300 after interpreting data from the photodiode sensor 204. In this manner, when a welding arc is present, the visor lens 202 may be darkened to protect the eyes of the operator 102, and when the welding arc is not present the visor lens 202 may be lightened so that the operator 102 can see the surrounding environment.

In some examples, the adaptable lens 214 may comprise an optofluidic lens having a liquid lens chamber. In some example, the adaptable lens 214 may be configured to adjust its focal length and/or radius of curvature in response to electrowetting. In some examples, the electrowetting may be triggered by one or more electrical signals (e.g., from the smart module circuitry 300 and/or control inputs 208). In some examples, the electrical signal(s) may be delivered to the adaptable lens 214 in response to adjustment of one or more control inputs 208. In some examples, the module circuitry 300 may interpret settings entered using the control inputs 208 and deliver signal(s) to the adaptable lens 214 indicative of the appropriate configuration. For example, an operator 102 may enter numbers from an eye exam or prescription (e.g., corresponding to OD, OS, OU, etc.), and the module circuitry 300 may translate this into the appropriate configuration for the adaptable lens 214.

In some examples, the module circuitry 300 may be configured to automatically adjust the configuration of the adaptable lens 214 to correspond to saved settings of the operator 102. In some examples, the smart helmet module 200 may automatically detect the identity (and/or one or more identification characteristics) of the operator 102 (e.g., via sensor(s) 204), receive operator identification information (e.g., via control inputs 208), and/or otherwise identify the operator 102, and load the settings (and/or receive the settings from remote server(s) 108) after identifying the operator 102. In this way, an operator 102 may be able to easily adjust the optics of the adaptable lens 214 to correspond to their needs and/or desires (e.g., to compensate for poor eyesight, mimic corrective lenses, etc.). In some examples, the adaptable lens 214 may additionally allow operators 102 to avoid having to wear glasses underneath the welding helmet 104, and/or using one size fits all cheater magnification lenses.

In some examples, the display screen 216 may be a near-eye display. In some examples, the display screen 216 may be semi-transparent and/or configured to overlay information (e.g., virtual/simulated/holographic objects, guidance, messages, parameters, etc.) onto at least part of the surrounding environment that the operator 102 views through the visor lens 202. In some examples, information overlaid via the display screen 216 may include remaining power (e.g., battery life) of the smart helmet module 200, status of nearby welding equipment 106 in communication with the smart helmet module 200, status of a nearby PAPR 110 (e.g., filter status) in communication with the smart helmet module 200, and/or information (e.g., metrics, instructions, guidance, etc.) from weld and/or part tracking systems in communication with the smart helmet module 200.

In some examples, the display screen 216 may be part of the entire visor lens 202. In some examples, the display screen 216 may be part of only a portion of the visor lens 202, so as to be visible to only one eye and/or positioned over a portion (e.g., top/bottom/left/right) of one or both eyes. In some examples, the display screen 216 may cover the entirety of the visor lens 202, to be visible to and/or positioned over the entire visible range of both eyes. In some examples, the display screen 216 may be separate from the visor lens 202, and/or positioned between the operator 102 and the visor lens 202.

In some examples, the display screen 216 (and/or adaptable lens 214 and/or visor lens 202) may wrap around approximately (e.g., within 15-20 degrees of) 180 degrees of the welding helmet 104 and/or face of the operator 102, so as to provide one or more wide and/or panoramic views to the operator 102. In some examples, one or more optical sensors 204 may be configured to capture one or more images/videos of the surrounding environment in one or more different fields of view, and the one or more images/videos may be displayed on the display screen 216. In some examples, the one or more images/videos may be combined (e.g., by the module circuitry 300) to produce the panoramic view.

In some examples, the display screen 216 may be configured to convert electrical signals (e.g., from the smart module circuitry 300 and/or sensors 204) into optical information viewable by the operator 102. In some examples, the optical sensor(s) 204 may be controlled (e.g., via control input(s) 208) to zoom in and/or out (e.g., by moving the sensor(s) 204, changing focal length(s) of the sensor(s) 204, selecting input from one or more different sensors 204, etc.). In some examples, by using display screen 216 to superimpose information onto the visor lens 202, the welding helmet 104 may show a variety of mixed, virtual, and/or augmented reality views, displays, information, and/or interfaces, such as described, for example, in U.S. Pat. No. 10,448,692, issued on Oct. 22, 2019, and U.S. Pat. No. 10,380,911, issued on Aug. 13, 2019, the entirety of both being hereby incorporated by reference. In some examples, by displaying image(s)/video(s) captured by (e.g., zoomed in) optical sensor(s) 204, the operator 102 may be able to view enhanced detail that an unaided human eye would otherwise have difficulty discerning.

Figure 3:
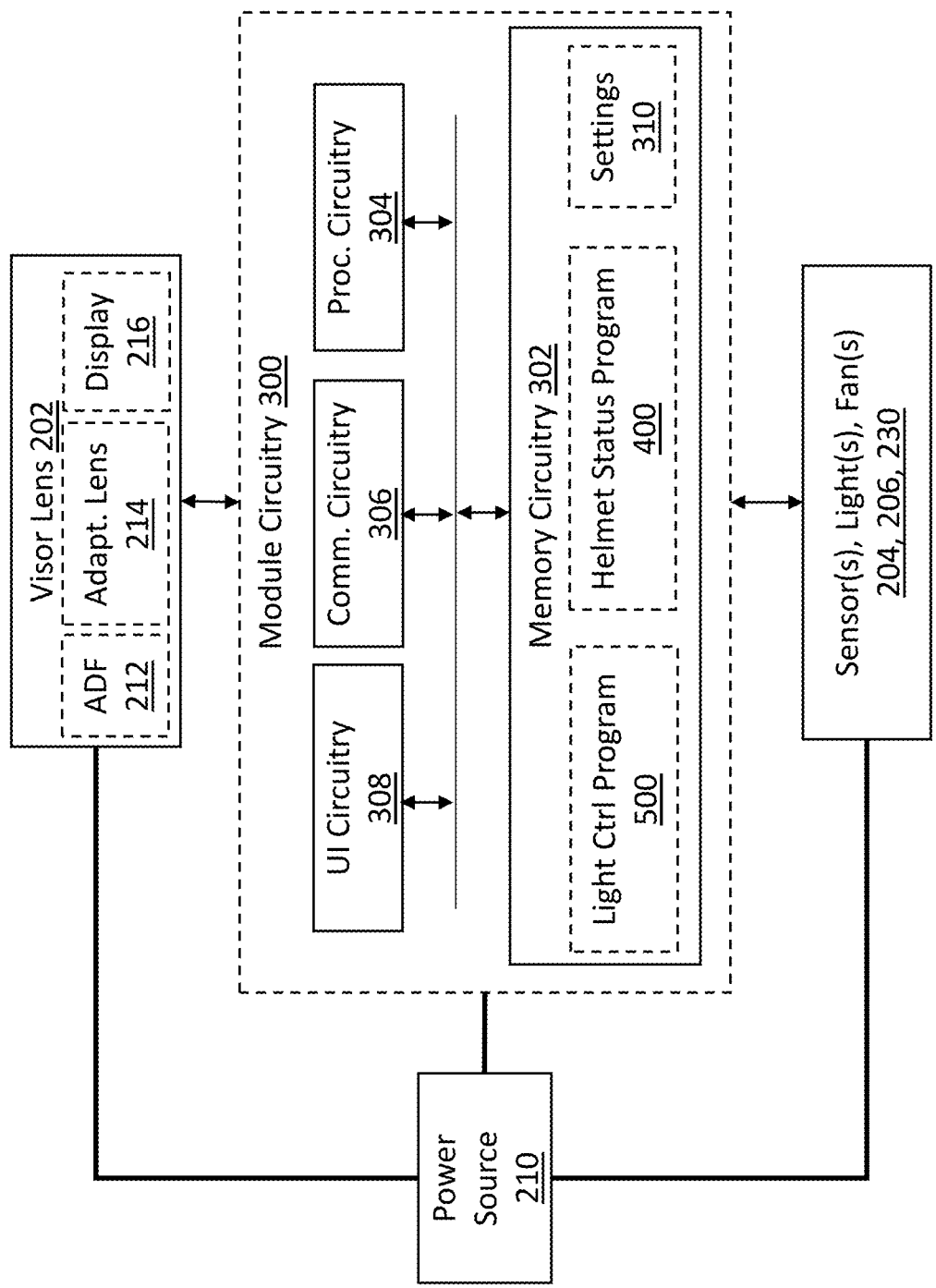
FIG. 3 is a block diagram showing example electrical components of the smart helmet module of FIG. 1, in accordance with aspects of this disclosure.

FIG. 3 is a block diagram showing example components of the module circuitry 300 of the smart helmet module 200, as well as interconnections between the components of the module circuitry 300 and other components of the smart helmet module 200. As shown, the module circuitry 300 includes memory circuitry 302, processing circuitry 304, communication circuitry 306, and user interface (UI) circuitry 308, interconnected with one another via a common electrical bus. The module circuitry 300 is also in electrical communication with the visor lens 202, the sensor(s) 204, the light(s) 206, and the fan(s) 230. As shown, the module circuitry 300, visor lens 202, sensor(s) 204, light(s) 206, and fan(s) 230 are powered by a power source 210 (e.g., a battery, power cell, etc.). While the power source 210, sensor(s) 204, and light(s) 206 are shown as separate from the module circuitry 300 in the example of FIG. 3, in some examples, the power source 210 and/or some or all of the sensors 204 and/or lights 206 may be part of the module circuitry 300. In some examples, one or more of the sensors 204 may be configured to detect a remaining power (and/or voltage) level of the power source 210, and/or a current output power (and/or current/voltage) of the power source 210. In some examples, the power source 210 may be configured to connect to and/or receive power from an external source (e.g., welding equipment 106, PAPR 110, mains power, etc.), either to directly power the smart helmet module 200 or to recharge the power source 210 (e.g., via wired or wireless recharging).

In some examples, the UI circuitry 308 may be coupled to the control inputs 208 (and/or certain mechanical and/or electromechanical aspects of the control inputs 208). In some examples, the UI circuitry 308 may comprise one or more drivers for the control inputs 208. In some examples, the UI circuitry 308 may be configured to generate one or more signals representative of input received via the control inputs 208. In some examples, the UI circuitry 308 may also be configured to generate one or more outputs (e.g., via the via the control inputs 208) in response to one or more signals (e.g., received via the bus).

In some examples, the communication circuitry 306 may include one or more wireless adapters, wireless cards, cable adapters, wire adapters, dongles, radio frequency (RF) devices, wireless communication devices, Bluetooth devices, IEEE 802.11-compliant devices, WiFi devices, cellular devices, GPS devices, Ethernet ports, network ports, lightning cable ports, cable ports, etc. In some examples, the communication circuitry 306 may be configured to facilitate communication via one or more wired media and/or protocols (e.g., Ethernet cable(s), universal serial bus cable(s), etc.) and/or wireless mediums and/or protocols (e.g., near field communication (NFC), ultra high frequency radio waves (commonly known as Bluetooth), IEEE 802.11x, Zigbee, HART, LTE, Z-Wave, WirelessHD, WiGig, etc.).

In some examples, the communication circuitry 306 may be configured to handle communications between the smart module circuitry 300 and other devices internal to, and/or external of, the smart helmet module 200. For example, the communication circuitry 306 may receive one or more signals (e.g., from the welding equipment 106, sensor(s) 204, PAPR 110, remote server(s) 108, visor lens 202, etc.) decode the signal(s), and provide the decoded data to the electrical bus. As another example, the communication circuitry 306 may receive one or more signals from the electrical bus (e.g., representative of one or more virtual objects), encode the signal(s), and communicate the encoded signal(s) to the visor lens 202. In some examples, the communication circuitry 306 may act as a signal beacon, broadcasting an electromagnetic signal that may be detected by devices within the area.

In some examples, the smart helmet module 200 may communicate (e.g., via communication circuitry 306) with, output data pertaining to, and/or interact with weld/part tracking, monitoring, and/or guidance systems (e.g., implemented via remote server(s) 108 and/or welding equipment 106), such as described, for example, in U.S. Pat. No. 6,583,386, issued on Jun. 24, 2003, U.S. Pat. No. 10,661,373, issued on May 26, 2020, and U.S. patent application Ser. No. 16/363,748, filed Mar. 25, 2019, the entirety of each being hereby incorporated by reference.

In some examples, the processing circuitry 304 may comprise one or more processors, controllers, and/or graphical processing units (GPUs). In some examples, the processing circuitry 304 may comprise one or more drivers for the sensor(s) 204 and/or visor lens 202. In some examples, the processing circuitry 304 may be configured to execute machine readable instructions stored in the memory circuitry 302.

In the example of FIG. 3, the memory circuitry 302 includes (and/or stores) operator settings 310, a helmet status program 400, and a light control program 500. While shown as part of the memory circuitry 302 in the example of FIG. 3, in some examples, the operator settings 310 may be received from the remote server(s) 108 instead of, or in addition to, being stored in memory circuitry 302. In some examples, the operator settings 310 may comprise customized (or default) settings of the ADF 212, adjustable lens 214, display screen 216, control inputs 208, lights 206, sensors 204, and/or other aspects of the smart helmet module 200 for a particular operator 102. In some examples, the processing circuitry 304 may access, load, and/or implement the settings 310 after identifying the operator 102.

In some examples, the helmet status program 400 and light control program 500 may comprise machine readable instructions configured for execution by the processing circuitry 304. In some examples, the helmet status program 400 and light control program 500 may comprise state machines. In some examples, the helmet status program 400 and the light control program 500 may be implemented via discrete circuitry (e.g., of the processing circuitry 304) rather than, or in addition to, being part of (and/or stored in) the memory circuitry 302. In some examples, the helmet status program 400 and light control program 500 may execute simultaneously and/or in parallel.

Figure 4:
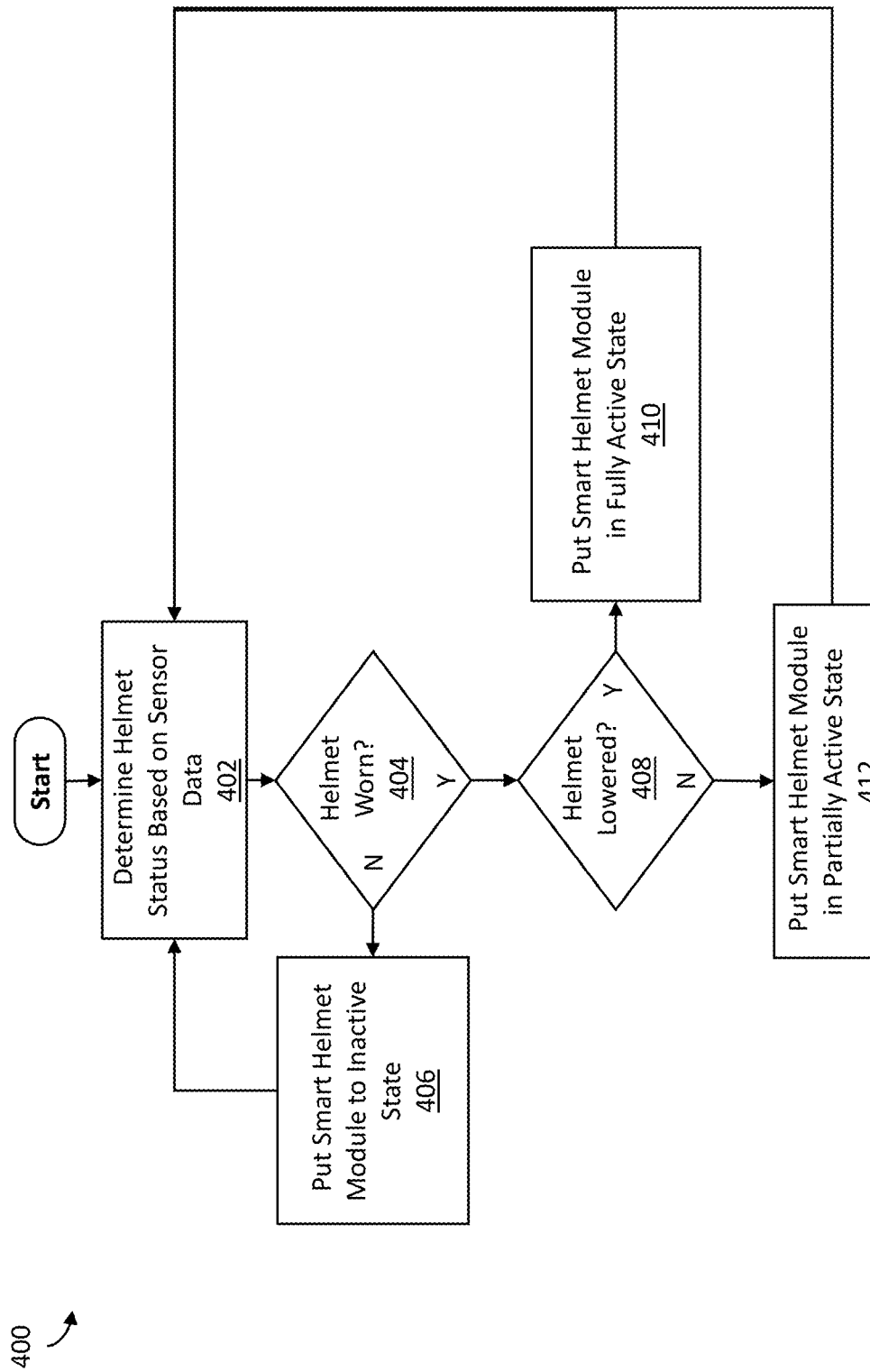
FIG. 4 is a flow diagram illustrating an example operation of a helmet status program of the smart helmet module of FIG. 1, in accordance with aspects of this disclosure.

FIG. 4 is a flowchart illustrating operation of an example helmet status program 400. As shown, the helmet status program 400 begins at block 402, where the helmet status program 400 determines the status of the welding helmet 104. In some examples, determining the status of the welding helmet 104 may comprise determining whether the helmet 104 is being worn or not worn, and/or whether the helmet 104 is being worn up in the raised position (e.g., as shown in FIG. 2b) or down in the lowered position (e.g., as shown in FIG. 2c).

In some examples, whether the welding helmet 104 is being worn or not worn may be determined based on data obtained from the sensor(s) 204. For example, a thermal sensor 204 (e.g., positioned in/on, and/or attached to, the suspension 132 of the helmet 104) may detect increased heat from the operator 102 when the helmet 104 is being worn, and decreased heat when the helmet is not worn. As another example, a simple mechanical switch sensor 204 (e.g., positioned in/on, and/or attached to, the suspension 132 of the helmet 104) may be actuated when the helmet 104 is being worn. As another example, a capacitive sensor 204 (e.g., positioned in/on, and/or attached to, the suspension 132 of the helmet 104) may detect contact from skin of an operator 102 when the helmet 104 is being worn, and no contact when the helmet 104 is not being worn.

As another example, an optical sensor 204 (e.g., an IR sensor 204) retained in the suspension 132 and/or helmet shell 130 may detect an optical signal (e.g., a light) emitted by a light 206 that is also retained in the suspension 132 and/or helmet shell 130 when the welding helmet 104 is not being worn. In such an example, the optical sensor 204 may be retained in a strap of the suspension 132 that wraps around the back of the head of an operator 102 when the welding helmet 104 is being worn, and the light 204 may be retained in a strap of the suspension 132 that wraps around the crown or forehead (or vice versa). In such an example, the light 206 may be directed at the sensor 204 across a gap that would normally be filled by the head of an operator 102 when the welding helmet 104 is worn. Thus, if the sensor 204 detects the optical signal it may determined that the helmet 104 is not being worn, because the head of the operator 102 would have interrupted the optical signal if the welding helmet 104 was being worn.

In some examples, the sensor 204 and/or light 206 may be positioned differently, so long as the optical signal is sent across a space that would normally be filled by the head of the operator 102 when the welding helmet 104 is worn. In some examples, the light 206 and sensor 204 may be positioned at the same location (and/or in the same device) and a reflector may be retained in the suspension 132 and/or helmet shell 130 to reflect the optical signal back to the sensor 204 when not interrupted by the head of the operator 102.

In some examples, whether the welding helmet 104 is being worn raised or lowered may be determined based on data obtained from the sensor(s) 204. For example, a carbon dioxide sensor 204 may detect increased carbon dioxide levels, an airflow sensor 204 may detect increased airflow levels, and/or an oxygen sensor 204 may detect decreased oxygen levels, when the helmet 104 is being worn down over the face of the operator 102. As another example, an IMU sensor 204 may detect an acceleration (and/or rotation) of the helmet 104 indicative of movement of an operator 102 wearing the helmet 104, and/or of the helmet 104 between up/down positions. As another example, two coordinated IMU sensors 204, one in the helmet shell 130 and the other in the suspension 132, may detect relative force vectors from which the arc time tracking program 400 can determine whether the welding helmet 104 is in the raised or lowered position.

As another example, a potentiometer and/or encoder sensor 204 retained in/on the suspension 132 may be configured to detect different rotational positions of the helmet shell 130 with respect to the side attachment point(s) 134 of the suspension 132 output a voltage and/or electrical signal representative of the detected rotational position. In such an example, and the helmet status program 400 may translate the output from the potentiometer and/or encoder sensor 204 as indicative of the helmet 104 being in a raised or lowered position. As another example, a reed switch sensor 204 retained in the middle strap of the suspension 132 may be actuated by a magnet of the smart helmet module 200 that comes within proximity of the reed switch sensor 204 when the helmet 104 is raised. As another example, a mechanical switch sensor 204 retained in/on a rear strap of the suspension 132 may be actuated by the helmet shell 130 when the helmet 104 is in the raised position.

As another example, an optical sensor 204 (e.g., an IR sensor 204) retained in/on one side of helmet shell 130 may detect an optical signal (e.g., a light) emitted by a light 206 that is retained in/on the other side of the helmet shell 130 when the helmet 104 is in the raised position. The light 206 may be directed at the sensor 204 (and/or the sensor 204 and light 206 may be positioned) such that the optical signal is emitted across a gap that would normally be filled by the head of an operator 102 when the welding helmet 104 is worn in the lowered position. For example, the light 206 and/or sensor 204 may be positioned on opposite sides of the lower helmet shell 130 at an approximate height of the chin and/or cheek of the operator 102 when the helmet 104 is worn in the lowered position (see, e.g., FIG. 2b). In some examples, the light 206 and sensor 204 may be positioned at the same location (and/or in the same device) and a reflector may be retained in/on the helmet shell 130 to reflect the optical signal back to the sensor 204 when not interrupted by the head of the operator 102. In such examples, the optical signal would be interrupted by the operator 102 when the helmet 104 is worn in the lowered position. However, when the helmet 104 is raised (e.g., as in FIG. 2c), the optical signal would no longer be blocked by the operator 102, and the sensor 206 would detect the signal. Thus, it may be determined that the helmet is being worn in the raised position if the sensor 204 detects the optical signal, because the head of the operator 102 would have interrupted the optical signal if the welding helmet 104 was being worn in the lowered position.

In some examples, the sensor 204 might also detect the optical signal if no operator is wearing the helmet 104 at all. However, such a situation may be avoided by first verifying that an operator 102 is wearing the helmet 104 (i.e., using a different method). Alternatively, this arrangement may be used to quickly verify that the helmet 104 is both being worn and being worn lowered down over the face of the operator 102, as the optical signal would be detected by the sensor 204 if either were not the case.

In the example of FIG. 4, the helmet status program 400 proceeds to block 404 after block 402. At block 404, the helmet status program 400 determines whether the data from the sensor(s) 204 indicates that the helmet 104 is being worn or not. For example, if the data from the sensor(s) 204 is indicative of detected heat, carbon dioxide, acceleration, and/or rotation above a (e.g., stored) threshold, the helmet status program 400 may determine that the helmet 104 is being worn. As another example, the helmet status program 400 may determine the helmet 104 is being worn if the mechanical switch sensor 204 and/or capacitive sensor 204 have detected contact, or if a light sensor 204 does not detect light directed across a headspace of the helmet 104.

In the example of FIG. 4, the helmet status program 400 proceeds to block 406 after block 404 if the helmet status program 400 determines the helmet 104 is not being worn. At block 406, the helmet status program 400 puts the smart helmet module 200 in an inactive state and/or low power state. In such a state, the smart helmet module 200 may refrain from certain functions to save power.

For example, in an inactive state and/or low power state the smart helmet module 200 may disable and/or deactivate the display screen 216, disable/deactivate some or all control inputs 208, disable/deactivate some or all of the functions relying on the control inputs 208 (e.g., voice commands), disable/deactivate some or all of the lights 206, disable/deactivate some or all sensors 204, disable/deactivate the ADF 212, disable/deactivate (and/or refrain from configuring) the adaptable lens 214, disable/deactivate the fan(s) 230, disable/deactivate the UI circuitry 308, disable/deactivate the PAPR 110 and/or a blower of the PAPR 110 (e.g., via one or more communication signals), disable/deactivate one or more welding accessories 140 (e.g., via one or more communication signals), disable/deactivate the communication circuitry 306, and/or disable/deactivate the power source 210.

In some examples, the smart helmet module 200 may additionally, or alternatively, limit operation of certain components, or operate certain components in a lower power mode, during the inactive and/or low power state of block 406. For example, the smart helmet module 200 may limit the information that may be shown via the display screen 216, limit the speed of the fan(s) 230, limit the intensity of (e.g., dim) one or more lights 206, limit the ability of the operator 102 to progress through steps of a weld guidance/monitoring system (e.g., via communication(s) with the remote server(s) 108), limit the ability of the communication circuitry 306 to communicate with (and/or remotely control) certain instruments (e.g., the welding equipment 106, the remote server(s) 108, and/or one or more of the welding accessories 140), limit the operational abilities (e.g., put in a sleep or lower power mode) of certain instruments (e.g., one or more of the welding accessories 140), and/or limit the power output of the power source 210 (e.g., put in a low power or sleep mode). As another example, the welding-type power supply 118, wire feeder 120, and/or gas supply 122 (or a corresponding gas valve) may be put in a low power/speed/flow mode. In some examples, the smart helmet module 200 may completely deactivate/disable a component that was previously only limited if a threshold amount of time passes with no (e.g., contradictory) input and/or change in worn status. As shown, the helmet status program 400 returns to block 402 after block 406.

In the example of FIG. 4, the helmet status program 400 proceeds to block 408 after block 404 if the helmet status program 400 determines the helmet is being worn. At block 408, the helmet status program 400 determines whether the data from the sensor(s) 204 indicates that the helmet 104 is being worn lowered down over the face of the operator 102, or raised up above the face of the operator 102.

For example, if the helmet status program 400 has determined that the helmet 104 is being worn, but the data from the sensor(s) 204 indicates that the carbon dioxide and/or airflow levels are below the threshold, the helmet status program 400 may determine that the helmet 104 is being worn raised rather than lowered. On the other hand, if the carbon dioxide and/or airflow levels are above the threshold, the helmet status program 400 may determine the helmet 104 is being worn lowered rather than raised. As another example, if the reed switch sensor 204 in the middle strap of the suspension 132 has been actuated, or the mechanical switch sensor 204 in the rear strap of the suspension 132 has been actuated, the helmet status program 400 may determine the helmet is being worn raised rather than lowered.

As another example, the helmet status program 400 may determine whether the helmet 104 is being worn lowered or raised based on whether an optical sensor 204 retained in/on one side of helmet shell 130 detects an optical signal emitted by a light 206 that is retained in/on the other side of the helmet shell 130. As another example, the helmet status program 400 may use data from a potentiometer and/or encoder sensor 204 to determine whether the helmet is being worn raised or lowered. As another example, once the helmet status program 400 determines that the helmet 104 is being worn raised or lowered, the helmet status program 400 may determine whether the operator 102 has moved the helmet to the other position based on data from the IMU sensor(s) 204, and keep track of the state of the helmet 104 in that way.

In the example of FIG. 4, the helmet status program 400 proceeds to block 410 after block 408 if the helmet status program 400 determines that the helmet 104 is being worn lowered down over the face of the operator 102. In some examples, the helmet status program 400 may also proceed to block 410 after block 408 if the helmet status program 400 cannot determine whether the helmet 104 is being worn lowered or raised. At block 410, the helmet status program 400 puts the smart helmet module 200 in a fully activated state.

In some examples, all (or most) functions and/or components of the smart helmet module 200 (and/or devices in communication with the smart helmet module 200) may be fully activated/enabled in the fully activated state. In some examples, the fully activated state may be correlated with a higher power usage. However, in some examples, a few functions of the smart helmet module 200 may still be disabled in the fully activated state. For example, one or more lights 206 (e.g., retained in suspension 130 or on lower part of helmet shell 130) may be deactivated in the fully activated state. As another example, the cooling system 152 may be deactivated in the fully activated state (e.g., so as not to disrupt shielding gas flow of an impending welding operation). As shown, the helmet status program 400 returns to block 402 after block 410.

In the example of FIG. 4, the helmet status program 400 proceeds to block 412 after block 408 if the helmet status program 400 determines that the helmet is being worn raised up above the head of the operator 102. At block 412, the helmet status program 400 puts the smart helmet module 200 in a partially activated state. In some examples, some functions and/or components of the smart helmet module 200 (and/or devices in communication with the smart helmet module 200) may be fully activated/enabled in the partially activated state, while others may be partially activated/enabled, limited, or completely deactivated/disabled (e.g., similar or identical to that which is discussed above with respect to block 406).

For example, the UI circuitry 308 may be disabled while the remaining module circuitry 300 is fully enabled when the smart helmet module 200 is in a partially activated state. As another example, some or all of the exterior lights 206 and/or sensors 204 may be disabled, while the lights 206 and/or sensors 204 interior to the welding helmet 104 remain active. As another example, the visor lens 202 may be deactivated, disabled, powered down, and/or put in a low power state. In some examples, the partially activated state may be correlated with moderate power usage. As shown, the helmet status program 400 returns to block 402 after block 412.

In some examples, the helmet status program 400 may communicate the status of the welding helmet 104 to the welding equipment 106, remote server(s) 108, welding accessories 140, and/or welding torch 114 periodically, at certain times, and/or when welding is attempted or performed. In some examples, a signal beacon of the smart helmet module 200 (and/or a remote beacon 148) may be activated and/or configured to broadcast the status of the welding helmet 104. In some examples, the remote beacon 148 may output a perceptible notification (e.g., combination of lights, sound, etc.) representative of the operator 102 not being ready for welding when the helmet 104 is not worn or worn in a raised position. In some examples, the remote beacon 148 may output a different perceptible notification (e.g., combination of lights, sound, etc.) representative of the operator 102 being ready for welding when the helmet 104 is worn in a lowered position (e.g., so the operator 102 and/or others are aware). In some examples, a power level of the power source 210 and/or the ADF 212 (or other ADF) may also be communicated and/or verified to be above a threshold when communicating ready for welding status.

In some examples, the welding equipment 106 and/or welding torch 114 may be disabled unless the helmet status program 400 communicates the status of the welding helmet 104 as being worn lowered down over the face of the operator 102 (and/or having an above threshold power level). In some examples, a front panel interface of the welding equipment 106 may be disabled when the helmet 104 is being worn and/or worn down over the face of the operator 102 (e.g., so that the welding equipment 106 may only be controlled via the helmet 104). In some examples, the smart helmet module 200 may log and/or record (e.g., via memory circuitry 302) the status of the welding helmet 104 periodically, at certain times, and/or when welding is attempted or performed. In some examples, a weld/part monitoring, guidance, and/or tracking system (e.g., implemented via the remote server(s) 108) may further log and/or record the status of the welding helmet 104 periodically, at certain times, and/or when welding is attempted or performed.

Figure 5:
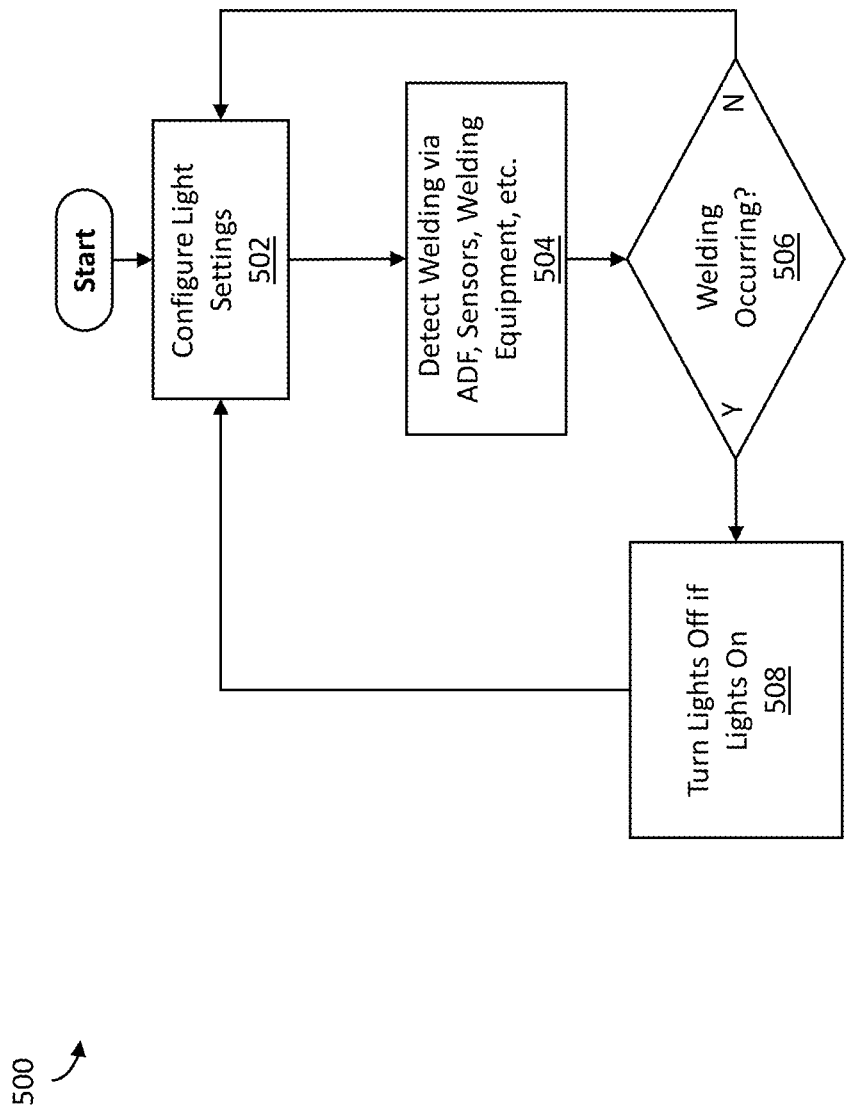
FIG. 5 is a flow diagram illustrating an example operation of a lighting control program of the smart helmet module of FIG. 1, in accordance with aspects of this disclosure.

FIG. 5 is a flowchart illustrating operation of an example light control program 500. As shown, the light control program 500 begins at block 502. At block 502, the light control program 500 configures the lights 206 based on user input (e.g., received via control inputs 208), operator settings 310, and/or the state of the smart helmet module 200. For example, the light control program 500 may configure whether the lights 206 (and/or which lights 206) are on/off, the intensity of the lights 206, the color of the lights 206, and/or other characteristics of the lights 206. In some examples, the (e.g., exterior) light(s) 206 may be turned on at block 502 by default (e.g., in the absence of contrary input) and/or if an ambient detected light is below a threshold.

In some examples, the light control program 500 may also configure other components of the smart helmet module 200 at block 502 based on user input (e.g., received via control inputs 208), operator settings 310, and/or the state of the smart helmet module 200. For example, the light control program 500 may (e.g., by default) activate and/or configure the display screen 216 to display images/videos captured by the optical sensors 204.

In the example of FIG. 5, the light control program 500 proceeds to block 504 after block 502. At block 504, the light control program 500 detects whether welding is occurring in the surrounding environment (e.g., based on data from the visor lens 202, sensor(s) 204, welding equipment 106, and/or welding torch 114). For example, the light control program 500 may determine that there is welding (and/or a welding arc) if the ADF 212 is darkened, if the amount of ambient light is sufficient to warrant darkening the ADF 212, if some other environmental characteristic (e.g., sound, heat, smoke, chemical composition, etc.) detected by a sensor 204 is above a threshold, if there is a non-trivial (e.g., over a threshold amount of) wire feed speed, current, and/or voltage, and/or if the trigger of the torch 114 is actuated.

In the example of FIG. 5, the light control program 500 proceeds to block 506 after block 504. At block 506, the light control program 500 determines whether welding is occurring based on the detections at block 504. As shown, the light control program 500 returns to block 502 if there is no welding. In some examples, the light control program 500 may also turn on and/or increase the intensity of one or more lights 206 if there is no welding. In some examples, the light control program 500 may further activate, deactivate, and/or readjust (e.g., back to prior/default configuration) one or more other components that may have been previously deactivated, activated, and/or adjusted when welding was occurring.

In the example of FIG. 5, the light control program 500 proceeds to block 508 if welding is determined to be occurring. At block 508, the light control program 500 turns off (or substantially dims) some or all of the lights 206. In some examples, this deactivation of the lights 206 may help to save power in situations where illumination from the lights 206 would make only a trivial (if any) difference in view of the illumination already being provided (e.g., due to a welding arc). As shown the light control program 500 returns to block 502 after block 508.

In some examples, the light control program 500 may also adjust certain other functions and/or components of the smart helmet module 200 depending on whether welding is occurring (and/or a welding arc is present). For example, the light control program 500 may adjust which sensors 204 are used, such as by choosing to activate or use one or more logarithmic optical sensors 204 or linear optical sensors 204 depending on whether welding is occurring or not (and/or whether a welding arc is present or not), or selecting one or more optical sensors 204 with higher or lower sampling rates depending on whether welding is occurring or not (and/or whether a welding arc is present or not). As another example, the light control program 500 may adjust characteristics of one or more sensors 204 based on whether a welding is occurring, such as by changing the sampling rate of one or more optical sensors 204 to be higher or lower depending on whether welding is occurring or not (and/or whether a welding arc is present or not). In some examples, the light control program 500 may adjust characteristics (e.g., higher or lower sampling rate) of one or more sensors 204 based on the type of welding that is occurring (e.g., MIG v. pulse), and/or properties (e.g., pulse frequency) of the welding that is occurring, such as may be communicated from the welding equipment 106, for example.

In some examples, the light control program 500 may activate the fan 230 (and/or a remote cooling system 152) at block 508 in response to detecting that welding is occurring. In some examples, this may ensure that the operator 102 is cooled during welding operations. In some examples, the light control program 500 may deactivate the remote cooling system 152 at block 508 in response to detecting that welding is occurring (so as not to disrupt shielding gas flow).

In some examples, the light control program 500 may further turn off and/or deactivate the display screen 216, the remote display screen 150, the electronic eyewear 154, one or more control input/outputs 208 (e.g., speakers), and/or one or more optical sensors 204 at block 508 in response to detecting that welding is occurring. In some examples, the light control program 500 may put the display screen 216 and/or the electronic eyewear 154 into full transparency rather than deactivating. In some examples, this may allow a user to view (e.g., enhanced) images captured by the optical sensors 204 prior to welding, and view the welding operation through the light filter of the ADF 212 and/or the transparent faceplate 220 during welding.

In some examples, the light control program 500 may control the remote display screen 150 to output an alert, warning, and/or notification to other operators 102, or put the remote display screen 150 in a different state (e.g., dim state, power saving mode, etc.) rather than deactivating. In some examples, the light control program 500 may reduce the capabilities (e.g., lower the volume) of the one or more control input/outputs 208 (e.g., speakers) rather than deactivating.

In some examples, the light control program 500 may activate a signal beacon (and/or the remote beacon 148) at block 508 in response to detecting that welding is occurring. In some examples, the signal beacon may broadcast one or more signals to the surrounding area. In some examples, the signal(s) may be detectable by certain devices (e.g., welding accessories 140), and representative of a notification that welding is occurring. The devices (e.g., PAPR 110, fume extractor 142, remote cooling system 152, etc.) may activate in response to the signal or take some other appropriate action.

In some examples, the signal beacon may be implemented via the communication circuitry 306, one or more lights 206, and/or one or more control outputs 208 (e.g., speakers). In some examples, the signal(s) output by the signal beacon may be inaudible and/or invisible, which may help to avoid unnecessarily distracting the operator 102 during welding. For example, the signal(s) may be electromagnetic, optical outside the visible light spectrum (e.g., infrared, ultraviolet, etc.), and/or audio outside the audible frequency range (e.g., infrasonic, ultrasonic, etc.).

In some examples, the light control program 500 may send a specific activation command (e.g., via one or more signals sent by the communication circuitry 306) in response to detecting that welding is occurring. For example, the light control program 500 may command one or more of the welding accessories 140 to activate/deactivate in response to determining welding is occurring. In some examples, the operator settings 310 may indicate whether to broadcast and/or directly transmit (and/or which to which device(s) the transmission(s) should be directed).

In some examples, operation of the smart helmet module 200 may be dependent upon both the helmet status program 400 and light control program 500. To the extent conflicts arise, in some examples the helmet status program 400 may be determinative, while in some other examples, the light control program 500 may be determinative. In some examples, a positive function or operation (e.g., activation, enablement, transmission) may only occur if both the helmet status program 400 and light control program 500 agree on it (or at least neither seeks to prevent it).

The example smart helmet modules 200 described herein provide a system that can be easily placed into, and/or removed from, welding helmets 104 with no damage to the modules 200 or helmets 104. The smart helmet modules 200 are further configured to determine whether the retaining helmet 104 is being worn raised up, lowered down, or not at all, and adjust its state and/or operation accordingly. The smart helmet modules 200 additionally provide display screens 216 to view valuable information during (actual and/or simulated) welding operations, as well as adaptable lenses 214 that can be custom configured to fit the needs of an operator 102.

The present methods and/or systems may be realized in hardware, software, or a combination of hardware and software. The present methods and/or systems may be realized in a centralized fashion in at least one computing system, or in a distributed fashion where different elements are spread across several interconnected computing or cloud systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As used herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

As utilized herein, the terms "e.g.," and "for example" set off lists of one or more non-limiting examples, instances, or illustrations.

As used herein, the terms "coupled," "coupled to," and "coupled with," each mean a structural and/or electrical connection, whether attached, affixed, connected, joined, fastened, linked, and/or otherwise secured. As used herein, the term "attach" means to affix, couple, connect, join, fasten, link, and/or otherwise secure. As used herein, the term "connect" means to attach, affix, couple, join, fasten, link, and/or otherwise secure.

As used herein the terms "circuits" and "circuitry" refer to physical electronic components (i.e., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" and/or "configured" to perform a function whenever the circuitry comprises the necessary hardware and/or code (if any is necessary) to perform the function, regardless of whether performance of the function is disabled or enabled (e.g., by a user-configurable setting, factory trim, etc.).

As used herein, a control circuit may include digital and/or analog circuitry, discrete and/or integrated circuitry, microprocessors, DSPs, etc., software, hardware and/or firmware, located on one or more boards, that form part or all of a controller, and/or are used to control a welding process, and/or a device such as a power source or wire feeder.

As used herein, the term "processor" means processing devices, apparatus, programs, circuits, components, systems, and subsystems, whether implemented in hardware, tangibly embodied software, or both, and whether or not it is programmable. The term "processor" as used herein includes, but is not limited to, one or more computing devices, hardwired circuits, signal-modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing. The processor may be, for example, any type of general purpose microprocessor or microcontroller, a digital signal processing (DSP) processor, an application-specific integrated circuit (ASIC), a graphic processing unit (GPU), a reduced instruction set computer (RISC) processor with an advanced RISC machine (ARM) core, etc. The processor may be coupled to, and/or integrated with a memory device.

As used, herein, the term "memory" and/or "memory device" means computer hardware or circuitry to store information for use by a processor and/or other digital device. The memory and/or memory device can be any suitable type of computer memory or any other type of electronic storage medium, such as, for example, read-only memory (ROM), random access memory (RAM), cache memory, compact disc read-only memory (CDROM), electro-optical memory, magneto-optical memory, programmable read-only memory (PROM), erasable programmable read-only memory (EPROM), electrically-erasable programmable read-only memory (EEPROM), a computer-readable medium, or the like. Memory can include, for example, a non-transitory memory, a non-transitory processor readable medium, a non-transitory computer readable medium, non-volatile memory, dynamic RAM (DRAM), volatile memory, ferroelectric RAM (FRAM), first-in-first-out (FIFO) memory, last-in-first-out (LIFO) memory, stack memory, non-volatile RAM (NVRAM), static RAM (SRAM), a cache, a buffer, a semiconductor memory, a magnetic memory, an optical memory, a flash memory, a flash card, a compact flash card, memory cards, secure digital memory cards, a microcard, a minicard, an expansion card, a smart card, a memory stick, a multimedia card, a picture card, flash storage, a subscriber identity module (SIM) card, a hard drive (HDD), a solid state drive (SSD), etc. The memory can be configured to store code, instructions, applications, software, firmware and/or data, and may be external, internal, or both with respect to the processor.

The term "power" is used throughout this specification for convenience, but also includes related measures such as energy, current, voltage, and enthalpy. For example, controlling "power" may involve controlling voltage, current, energy, and/or enthalpy, and/or controlling based on "power" may involve controlling based on voltage, current, energy, and/or enthalpy.

As used herein, welding-type power refers to power suitable for welding, cladding, brazing, plasma cutting, induction heating, carbon arc cutting, and/or hot wire welding/preheating (including laser welding and laser cladding), carbon arc cutting or gouging, and/or resistive preheating.

As used herein, a welding-type power supply and/or power source refers to any device capable of, when power is applied thereto, supplying welding, cladding, brazing, plasma cutting, induction heating, laser (including laser welding, laser hybrid, and laser cladding), carbon arc cutting or gouging, and/or resistive preheating, including but not limited to transformer-rectifiers, inverters, converters, resonant power supplies, quasi-resonant power supplies, switch-mode power supplies, etc., as well as control circuitry and other ancillary circuitry associated therewith.

As used herein, a part, as used herein, may refer to a physical item that is prepared and/or produced through a welding-type process and/or operation, such as, for example, by welding two or more workpieces together. In some contexts, a part may refer to data stored in non-transitory memory that is representative of a physical item prepared and/or produced through a welding-type process and/or operation.

Disabling of circuitry, actuators, and/or other hardware may be done via hardware, software (including firmware), or a combination of hardware and software, and may include physical disconnection, de-energization, and/or a software control that restricts commands from being implemented to activate the circuitry, actuators, and/or other hardware. Similarly, enabling of circuitry, actuators, and/or other hardware may be done via hardware, software (including firmware), or a combination of hardware and software, using the same mechanisms used for disabling.

What is claimed is:

1. A welding helmet, comprising:
a light;
a sensor configured to detect a worn status of the welding helmet, the sensor configured to output a sensor signal representative of the worn status; and
processing circuitry configured to:
determine, based on the sensor signal, the worn status of the welding helmet, the worn status being indicative of the welding helmet being worn, worn in a raised position, worn in a lowered position, or not worn,
activate the light when the worn status is indicative of the welding helmet being worn in the raised position, and
deactivate the light when the worn status is indicative of the welding helmet being worn in the lowered position.

2. The welding helmet of claim 1, wherein the sensor comprises a thermal sensor, an optical sensor, a reed switch, a capacitive sensor, a carbon dioxide sensor, an oxygen sensor, a potentiometer, an encoder, or an accelerometer.

3. The welding helmet of claim 1, further comprising a power source configured to provide power to the light, the processing circuitry being further configured to configure the power source, or the provision of power from the power source, based on the worn status.

4. The welding helmet of claim 1, further comprising a visor lens, the visor lens comprising an adaptable lens, and the visor lens configured to adjust a focal length or radius of curvature of the adaptable lens.

5. The welding helmet of claim 4, wherein the processing circuitry is further configured to identify an identity of an operator wearing the welding helmet, the visor lens configured to adjust the focal length or radius of curvature of the adaptable lens based on the identity of the operator.

6. The welding helmet of claim 4, further comprising one or more control inputs, the one or more control inputs being configured to receive an operator input, and the visor lens configured to adjust the focal length or radius of curvature of the adaptable lens based on the operator input.

7. The welding helmet of claim 1, further comprising a helmet shell and a smart helmet module, the smart helmet module comprising the sensor, the light, the processing circuitry, and a mechanical linkage configured for removable attachment to the helmet shell, the mechanical linkage configured to allow the smart helmet module to move away from the helmet shell while still remaining attached to the helmet shell.

8. A welding helmet, comprising:
a visor lens comprising an adaptable lens, the visor lens being configured to adjust a focal length or radius of curvature of the adaptable lens;
a sensor configured to detect a worn status of the welding helmet, the sensor configured to output a sensor signal representative of the worn status; and
processing circuitry configured to:
determine, based on the sensor signal, the worn status of the welding helmet, the worn status being indicative of the welding helmet being worn, worn in a raised position, worn in a lowered position, or not worn, and
configure the visor lens based on the worn status.

9. The welding helmet of claim 8, further comprising a power source configured to provide power to the visor lens, or the sensor, the processing circuitry being further configured to configure the power source, or the provision of power from the power source, based on the worn status.

10. The welding helmet of claim 8, wherein the visor lens further comprises a display screen or an auto darkening filter, and the welding helmet further comprises a user interface comprising one or more input devices and one or more output devices.

11. The welding helmet of claim 8, wherein the processing circuitry is further configured to identify an identity of an operator wearing the welding helmet, the visor lens configured to adjust the focal length or radius of curvature of the adaptable lens based on the identity of the operator.

12. The welding helmet of claim 8, further comprising one or more control inputs, the one or more control inputs being configured to receive an operator input, and the visor lens configured to adjust the focal length or radius of curvature of the adaptable lens based on the operator input.

13. The welding helmet of claim 8, wherein the sensor comprises a first sensor, and the processing circuitry is configured to determine whether welding is occurring based on a sensor signal of a second sensor, a darkened or undarkened state of an auto-darkening filter (ADF), tool data received from a welding-type tool, or welding data received from welding-type equipment.

14. The welding helmet of claim 8, further comprising a helmet shell and a smart helmet module, the smart helmet module comprising the sensor, the visor lens, the processing circuitry, and a mechanical linkage configured for removable attachment to the helmet shell, the mechanical linkage configured to allow the smart helmet module to move relative to the helmet shell while still remaining attached to the helmet shell.

* * * * *